(12) United States Patent  (10) Patent No.: US 7,226,441 B2
Kulessa  (45) Date of Patent: Jun. 5, 2007

(54) CATHETER WITH BLOCK-OVERRIDING SYSTEM

(75) Inventor: Sigmund Kulessa, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 125 days.

(21) Appl. No.: 10/601,611

(22) Filed: Jun. 23, 2003

(65) Prior Publication Data

US 2004/0260249 A1  Dec. 23, 2004

(51) Int. Cl.
*A61M 25/00*  (2006.01)

(52) U.S. Cl. .................................... 604/523

(58) Field of Classification Search .............. 604/264, 604/266, 267, 268, 30, 6.09, 31, 32, 126, 604/33, 34, 35, 190
See application file for complete search history.

(56) References Cited

U.S. PATENT DOCUMENTS

| | | | | | |
|---|---|---|---|---|---|
| 623,022 | A | * | 4/1899 | Johnson | 607/116 |
| 2,930,378 | A | * | 3/1960 | Buyers | 604/45 |
| 3,841,308 | A | * | 10/1974 | Tate | 600/585 |
| 4,601,724 | A | * | 7/1986 | Hooven et al. | 604/264 |
| 4,968,306 | A | * | 11/1990 | Huss et al. | 604/264 |
| 5,360,414 | A | * | 11/1994 | Yarger | 604/264 |
| 5,797,898 | A | * | 8/1998 | Santini et al. | 604/890.1 |
| 5,893,841 | A | | 4/1999 | Glickman | |
| 5,897,534 | A | | 4/1999 | Heim et al. | |
| 6,123,861 | A | * | 9/2000 | Santini et al. | 216/2 |
| 6,551,838 | B2 | * | 4/2003 | Santini et al. | 436/174 |
| 6,571,125 | B2 | | 5/2003 | Thompson | |
| 6,749,574 | B2 | | 6/2004 | O'Keefe | |
| 2002/0115986 | A1 | | 8/2002 | Shadduck | |

* cited by examiner

*Primary Examiner*—Manuel Mendez
(74) *Attorney, Agent, or Firm*—Nutter, McClennen & Fish LLP

(57) ABSTRACT

A catheter is provided having a plurality of fluid entry ports formed therein and in communication with an inner lumen of the catheter. One or more of the fluid entry ports includes a fluid-permeable barrier extending there across. In a preferred embodiment, a set of conductive members is embedded in the wall of the catheter and connects each barrier to a control unit. In the event of blockage in the catheter, an external power source can non-invasively command the control unit to transmit an electric current to one or more of the barriers to dissolve or otherwise remove the barrier, thereby allowing fluid to once again flow through the catheter.

14 Claims, 3 Drawing Sheets

CATHETER WITH BLOCK-OVERRIDING SYSTEM

FIELD OF THE INVENTION

The present invention relates generally to a catheter having a system for overriding blockage or obstruction of the catheter pores.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the pores. The pores of the ventricular catheter can also be obstructed by debris, bacteria, or coagulated blood. Additionally, problems with the ventricular catheter can arise from overdrainage of the CSF, which can cause the ventricle walls to collapse upon the catheter and block the pores in the catheter wall, thereby preventing CSF drainage.

Some of these problems can be treated by backflushing, which is a process that uses the CSF present in the shunt system to remove the obstructing matter. This process can be ineffective, however, due to the small size of the pores of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the pores and the degree and extent to which the pores have been clogged.

Occluded ventricular catheters can also be repaired by cauterizing the catheter to remove blocking tissue, thereby reopening existing pores that have become occluded. Alternatively, new pores can be created in the catheter. These repairs, however, may be incapable of removing obstructions from the ventricular catheter depending on the location of the clogged pores. Additionally, the extent of tissue growth into and around the catheter can also preclude the creation of additional pores, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by simply removing the obstructed catheter from the ventricle, the growth of the choroid plexus and other tissues around the catheter and into the pores can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt system that minimizes or eliminates the risk of blockage or obstruction of the catheter pores, and reduces the need for repeated repair and/or replacement.

SUMMARY OF THE INVENTION

The present invention provides an implantable fluid management device which, in general, includes a catheter having a proximal end, a distal end, and an inner lumen extending therethrough. A plurality of fluid entry ports are formed in a sidewall of the catheter, in fluid communication with the inner lumen of the catheter, and a fluid-impermeable barrier extends across each of the fluid entry ports. The barrier is selectively removable with respect to each of the plurality of fluid entry ports. In one embodiment, the fluid entry ports are arranged in rows that extend around a circumference of the catheter and they are positioned longitudinally apart from one another. Each row preferably includes at least one fluid entry port.

In another embodiment, the device can include a microprocessor coupled to the catheter that is effective to selectively apply a stimulus to one or more of the barriers to remove the barrier, and a plurality of conductors that are effective to carry an electric current. Each conductor preferably extends from the microprocessor to one or more of the barriers. In use, the microprocessor is effective to initiate removal of the barrier in response to a signal received from a remote device. In an exemplary embodiment, the stimulus is an electric current, and the barrier is formed from a material selected from the group consisting of copper, gold, silver, and zinc.

In other aspects, the catheter can include a sensor disposed adjacent to one or more of the plurality of fluid entry ports. The microprocessor is preferably effective to initiate removal of the barrier upon detection of a particular condition detected by the sensor. In yet another embodiment, the catheter can include several filter members, wherein each filter member extends transversely to a longitudinal axis of the catheter member and is positioned between two rows of fluid entry ports. Alternatively, or in addition, a filter material can be disposed around an inner diameter of the catheter to essentially line the inner surface of the catheter.

In yet another embodiment, the present invention provides a method of maintaining fluid flow through a catheter. In general, a catheter is provided having an elongate member having a proximal end, a distal end, and an inner lumen extending therethrough. One or more fluid entry ports are formed in the elongate member and they are arranged in rows spaced apart from one another along the length of the elongate member. Each row preferably includes at least one fluid entry port. The catheter also includes a disintegratable barrier extending across each fluid entry port, with a row of barrier-free fluid entry ports adjacent the distal end of the elongate member. A control member is provided for selectively removing the barrier from each of the fluid entry ports. The method includes the steps of detecting a blockage of fluid-flow through the distal-most barrier-free row of fluid entry ports, activating the control member to remove the barrier from a row of fluid entry ports positioned just proximal to the distal-most row of fluid entry ports, and repeating the steps of detecting and activating as necessary.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
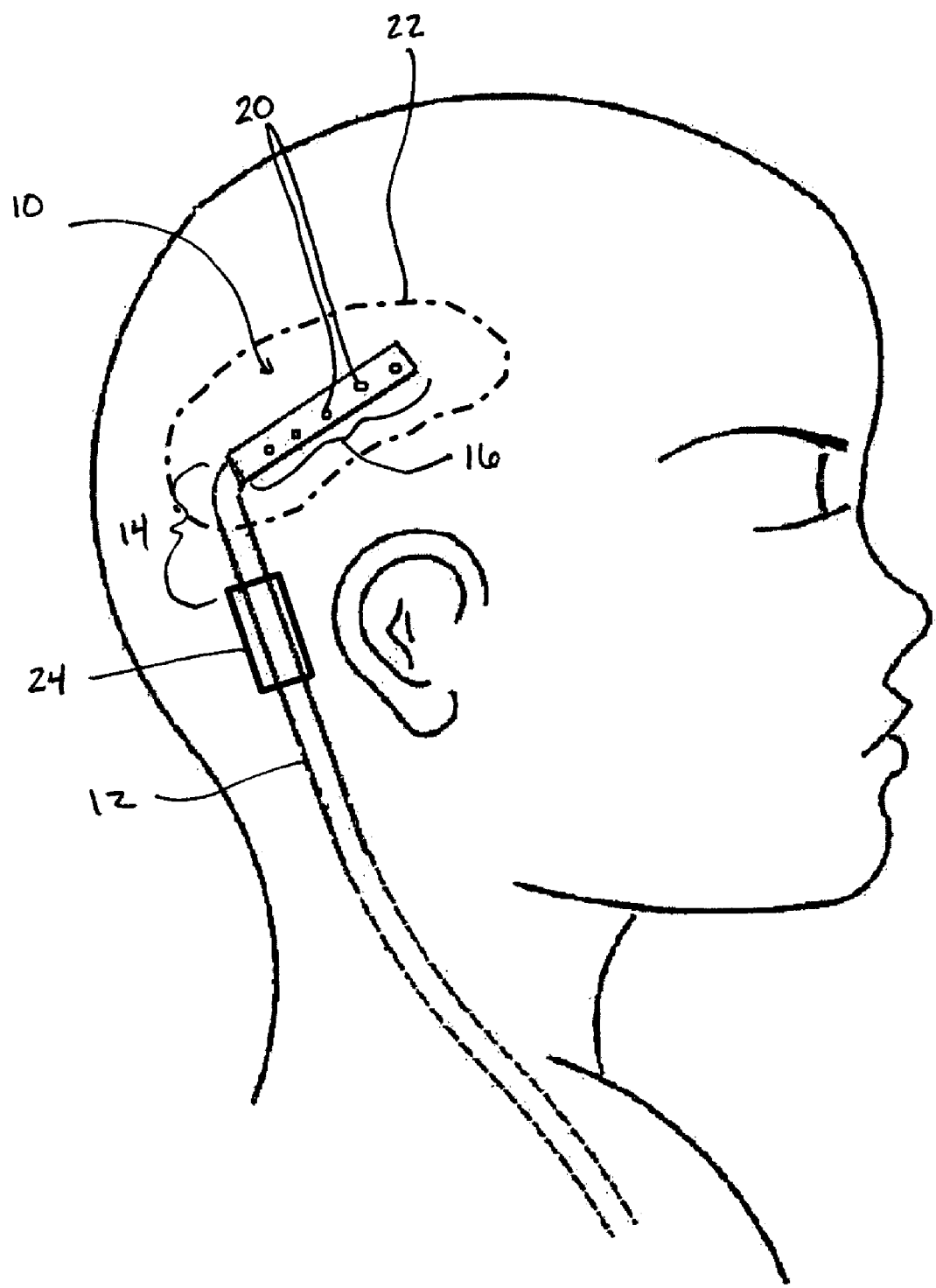
FIG. 1 is a perspective, semi-transparent illustration of a portion of a shunt device implanted within a patient's cerebral ventricle according to the present invention.

As shown in FIG. 1, the present invention provides a shunt device 10 that is useful for selectively clearing blockages that might occur after the device is implanted. In general, the device 10 includes an elongate catheter 12 having a proximal portion 14, a distal portion 16, and an inner lumen 18 (shown in FIG. 2) extending therebetween. At least one fluid entry port 20 is formed in the catheter 12 and is in communication with the inner lumen 18. The catheter 12 can be used for a variety of diagnostic and therapeutic procedures, including for the removal or introduction of fluid to a treatment site. In an exemplary embodiment, the catheter 12 is used for treating hydrocephalus. The distal portion 16 of the catheter 12 is implanted within one of the patient's cerebral ventricles 22, which contains cerebrospinal fluid (CSF), and the proximal portion 14 can either remain outside the patient's body to collect CSF, be the mated to another medical device, or it can be implanted at another location in the body where the CSF can be absorbed into the circulatory system.

Figure 2:
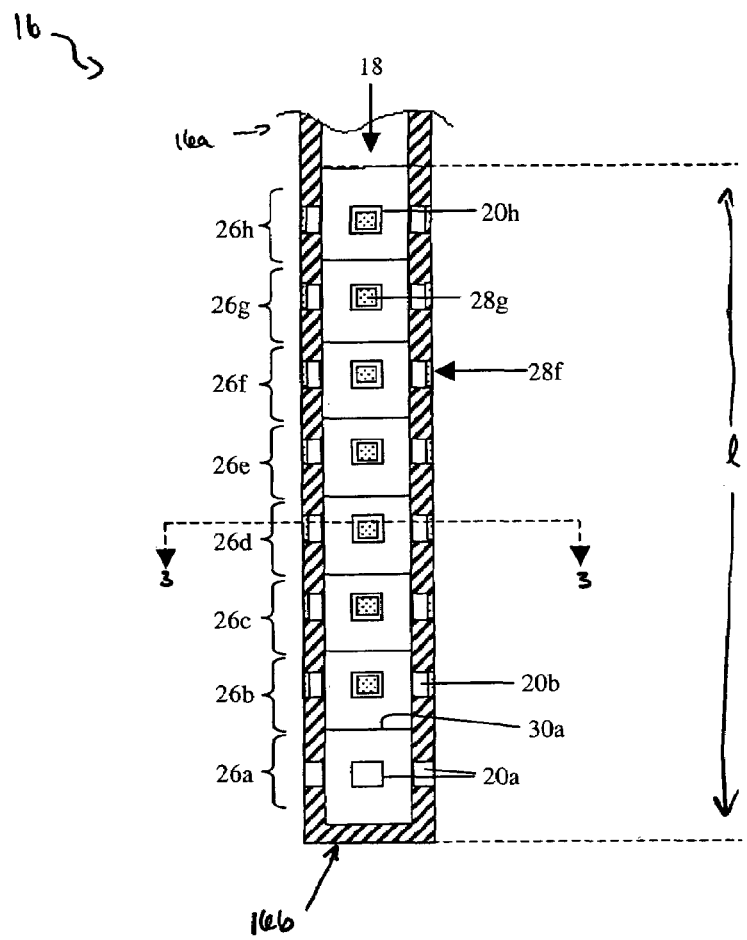
FIG. 2 is a cross-sectional view of a distal portion of a catheter in accordance with the present invention.

The catheter 12 can have virtually any shape and size, but is preferably a substantially elongate cylindrical member having at least one inner lumen 18 extending therethrough, as shown in FIG. 2. The proximal portion 14 of the catheter 12 can include an open or closed proximal end, depending on the intended use, and can optionally be adapted to mate to another medical device. In an exemplary embodiment, the proximal portion 14 has an open proximal end and is either implanted at another location within the patient's body that is adapted to receive CSF fluid from the cerebral ventricle, or is mated to a shunt valve 24 (FIG. 1) which is mated to another catheter that extends to a site in the patient's body. The shunt valve 24 is effective to regulate the flow of the CSF through the system. The distal portion 16 of the catheter 12 can also include an open or closed end, but preferably the distal-most end 16b is closed such that the inner lumen 18 terminates at a position proximal to the distal-most end of the catheter 12. This allows a stylet or similar device to be inserted into the catheter 12 to facilitate implantation of the device 10. The distal-most end 16b of the catheter 12 can optionally be rounded or conical to further facilitate insertion of the device 10 into a treatment site.

A person skilled in the art will appreciate that the configuration of the catheter 12 can vary, and the catheter 12 can include a variety of other features not described or illustrated herein. By way of non-limiting example, the catheter 12, or a portion thereof, can have a preconfigured shape, and can also optionally or alternatively include one or more secondary catheters that branch off from the primary catheter.

The catheter 12 also includes at least one fluid entry port 20 formed therein so as to be in fluid communication with the inner lumen 18. The size, shape, and position of the entry ports 20 can vary, but each entry port 20 should have a size and shape sufficient to allow fluid to flow therethrough and into or out of the inner lumen 18. The shape of each entry port 20 can be, for example, circular, oval, square, rectangular, etc. In an exemplary embodiment, each entry port 20 has a substantially circular shape. The diameter of each entry port 20 can also vary, but preferably the diameter is in the range of about 0.75 mm to 1.5 mm.

FIG. 2 illustrates an exemplary embodiment of a catheter 12 having one or more entry ports 20a-20h arranged in rows 26a-26h. For reference purposes, all features in a single row are labeled with the same suffix. The entry ports 20a-20h are longitudinally spaced apart from one another along a length L of the distal portion 16 of the catheter 12. Each row 26a-26h preferably includes at least one entry port 20a-20h formed therein. As shown in FIG. 2, and in FIG. 3 which illustrates a cross-section of row 26d, each row 26a-26h includes four entry ports 20a-20h (entry ports 20a-20h in the same row 26a-26h are labeled with the same reference number) that are positioned equidistant from one another. A person skilled in the art will appreciate that the catheter 12 can include any number of entry ports 20a-20h and/or rows 26a-26h, and that the entry ports 20 can be positioned anywhere along the length of the catheter 12. Moreover, the entry ports 20a-20h can have virtually any shape and size as long as they are effective to receive fluid flow therethrough.

Figure 3:
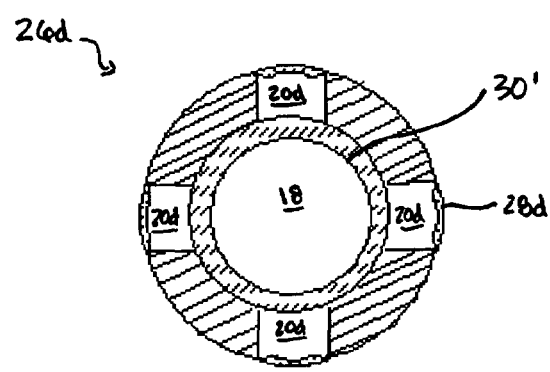
FIG. 3 is a cross-sectional view of the catheter shown in FIG. 2 taken across line 3-3.

Still referring to FIGS. 2 and 3, each entry port 20a-20h in the catheter 12 can also include a barrier 28b-28h disposed in or occluding the entry port 20a-20h. The barriers 28b-28h are preferably effective to prevent, at a minimum, the ingrowth of tissue through the entry port 20a-20h, and each barrier can be selectively removed during use of the device 10 by the application of an applied stimulus, as discussed in more detail below. The barriers 28b-28h can have a variety of configurations, and can be, for example, a cap, a membrane, a plug, or a film. The barriers 28b-28h can also be positioned in, on, or around any number of entry ports 20a-20h. As shown in FIG. 2, every entry port 20b-20h except the distal-most row of entry ports 20a is occluded by a barrier 28b-28h. This configuration is desirable since fluid will be forced to flow through the distal-most row 26a of entry ports 20a when the catheter 12 is implanted. Over time tissue may grow into the distal-most row 26a of entry ports 20a, thereby blocking the flow fluid. In order to avoid the need and to remove the catheter 12 or otherwise remove the blockage, the entry ports 20b in the row 26b just proximal to the distal-most row 26a can be opened by removing the barrier 28b to allow fluid to once again flow through the catheter 12. This procedure can be repeated as necessary to maintain the flow fluid through the catheter 12.

The barrier 28b-28h can be formed from a variety of materials that are suitable for in vivo use, and can be impermeable, permeable, or semi-permeable. In an exemplary embodiment, however, each barrier 28b-28h is preferably formed from a material that is capable of being selectively disintegrated or permeabilized by, for example, an applied stimulus (e.g., electric current, thermal, electrochemical, or mechanical means), as discussed below. Suitable materials include, for example, a thin metal membrane that is impermeable to the surrounding environment (e.g., body fluids). By way of non-limiting example, the barriers 28b-28h can be formed from copper, gold, silver, and zinc, or alternatively the barriers 28b-28h can be formed from biocompatible, conductive polymers or copolymers, or from one or more polymers or copolymers that are capable of controlled disintegration and/or permeabilization. Exemplary materials include, for example, polylactic acid (PLA) and polyglycolic acid (PGA).

The catheter 12 according to the present invention can also optionally include one or more filters disposed therein. The filters are effective to prevent the ingrowth of tissue therethrough and to collect other debris, while allowing fluid to flow through the inner lumen 18 of the catheter 12. While the filter(s) can have a variety of configurations, FIG. 2 illustrates one embodiment of catheter 12 having a filter 30a-30h disposed between each row 26a-26h and extending across the lumen 18 of the catheter 12. Each filter 30a-30h is effective to prevent tissue growth between rows 26a-26h. FIG. 3 illustrates a cross-sectional view of the distal portion 16 of the catheter 10 shown in FIG. 2. In this embodiment, however, the catheter 10 does not include transversely oriented filters 30a-30h, but rather it has a single filter 30' disposed around and lining the interior wall of the inner lumen 18 and extending along the distal portion 16 of the catheter 12'. As a result, the filter 30' acts a barrier to prevent tissue ingrowth through each entry port once the entry ports 20a-20h are opened. While the filter 30' is illustrated as a single filter 30', the filter 30' can optionally be formed as separate components covering each entry port 20a-20h. A variety of materials can be used formed the filter. Suitable materials include for example mesh, as well as filters formed from metals, polymers, and ceramics.

Figure 4:
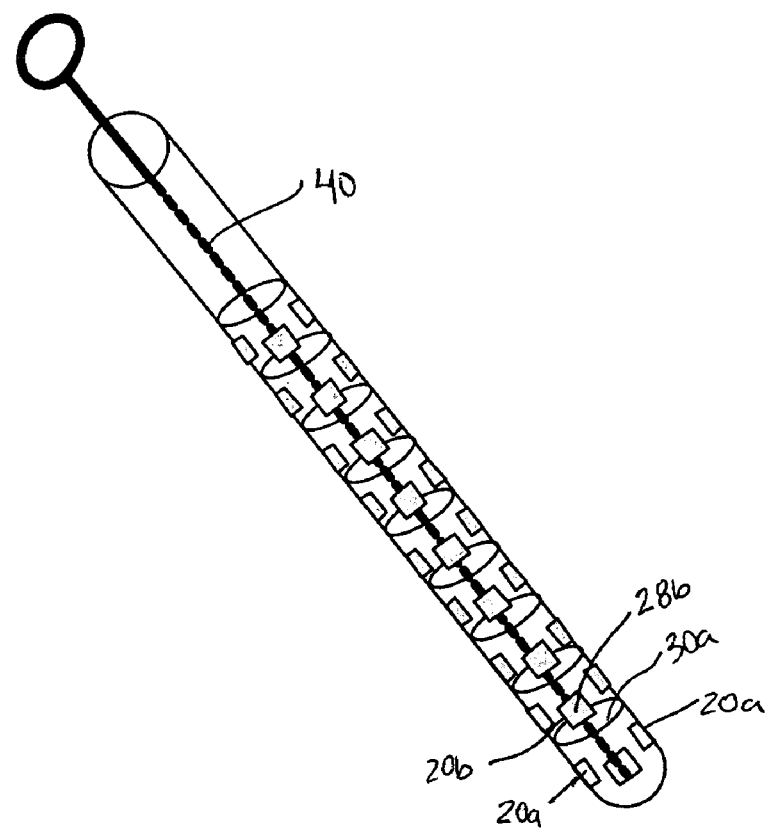
FIG. 4 is a perspective, transparent illustration of the catheter shown in FIG. 2 having a stylet disposed.

FIG. 4 illustrates the catheter 12 in use. As shown, a stylet 40 can be inserted through the catheter 12 to provide rigidity to the device for facilitating insertion of the device into a treatment site. Once the catheter 12 is implanted at the treatment site, the stylet 60 can be removed. The CSF is free to flow through the open fluid entry ports 20a, which, at least initially, are preferably the distal-most row 26a of entry ports 20a. The CSF then flows through the inner lumen 18 of the catheter 12, and to the proximal end of the catheter 12, which preferably includes a valve or other flow regulator mated thereto to control the drainage of the CSF. The CSF can optionally be deposited at a site in the body where it can be absorbed into the patient's circulatory system. Eventually, tissue and debris can grow into and block the entry ports 20a, thereby preventing or limiting the flow of CSF through the catheter 12. Instead of removing the blockage or replacing the catheter 12, the barrier 28b on each entry port 20b disposed in the row 26b just proximal to the distal most row 26a can be removed, thereby allowing fluid to once again flow through the catheter 12. This process can be repeated as blockage occurs to open up the next, downstream row of entry ports to allow the continuous and efficient flow of fluid through the catheter 12. A person skilled in the art will appreciate that while the entry ports are preferably opened starting with the distal most row 26a, any entry port can be opened in any order. Moreover, a person skilled in the art will appreciate that while the invention is described in connection with the use of a rigid stylet, an endoscope can additionally, or alternatively be used for visualizing the surgical site during implantation of the catheter. The endoscope can optionally provided rigidity to the catheter in place of the rigid stylet.

Removal of the barriers 28b-28h can be achieved using a variety of techniques. In an exemplary embodiment, however, as indicated above, each barrier 28b-28h is selectively removable in response to an applied stimulus, such as an electric potential that is transmitted to one or more the barriers 28b-28h. As a result, the barrier 28b-28h will oxidize and dissolve by an electrochemical reaction, exposing the contents of the reservoir to the surrounding environment. The electric potential can be carried to one or more of the metal barriers 28b-28h by way of a set of conductors (not shown) which are preferably embedded in the wall of the catheter. Each conductor can be coupled to a single barrier 28b-28h, a row 26b-26h of barriers 28b-28h, or in any other combination such that energy can be selectively transmitted via a conductor to remove a specific barrier 28b-28h or row of barriers 28b-28h.

Energy is preferably provided to the conductors using a control device that can be implanted in the patient's body, and an external programming device for communicating with the control device. The control device is preferably adapted to be implanted within the patient's body at a location near the catheter 10, for example, in the shoulder of the patient. The external programming device can then be used when necessary to communicate with the control device to selectively remove one or more barriers 28b-28h.

The control device can have a variety of configurations, but in general it is preferably in the form of a small metal housing that contains the microprocessor and communication circuitry. The power used to run the electronics in the control device and to dissolve the barriers 28b-28h can be supplied to the control device using a battery, but in an exemplary embodiment the control device utilizes a transcutaneous energy transfer (TET) device. TET devices are well known in the art, and in general, they simply require energy to be transferred from an external source, which is preferably part of the external programmer. This can be achieved by placing the external programming unit in proximity to the control device when power is needed. Additional components can be added to the control device depending on the desired mode of barrier actuation (e.g., thin film resistors for meltable barriers).

The microprocessor disposed within the control device can also have a variety of configurations, but preferably it has a small size with low or no power requirement. In use, the microprocessor is effective to translate the output from the external programming device into an address for the direction of power to a specific barrier 28b-28h in the catheter 10. While the microprocessor is described as being effective to response to the external programmer, the microprocessor can optionally be programmed to initiate the disintegration or permeabilization of the barrier in response to other conditions, including a specific time, or detection of a particular condition using a sensor such as a biosensor. By way of non-limiting example, the catheter 10 can optionally include a flow sensor that is integrated into or onto the device to detect the flow rate within the catheter 20. When the flow rate through the catheter reaches a certain threshold, the sensor sends a signal to the microprocessor to activate one or more entry ports. In response, the microprocessor directs power to the particular entry port(s) to disintegrate the corresponding barrier 28b-28h.

The external programming unit can also have a variety of configurations, but it should be effective to send a signal, such as radio frequency (RF) energy, microwaves, or ultrasound, to the control unit. The signal is received by the microprocessor where it is translated into one or more barrier 28b-28h addresses. Power is then directed to the entry port(s) having the appropriate address. Specific details regarding the external programming unit, and regarding other suitable techniques for manufacturing and using a device in accordance with the present invention, are disclosed in U.S. Pat. No. 6,551,838 of Santini, Jr. et al., which is incorporated herein by reference in its entirety.

A person skilled in the art will appreciate that a variety of other techniques can be used to selectively remove the barriers 28b-28h from one or more entry ports 28a-28h. By way of non-limiting example, the barriers 28b-28h can be adapted to disintegrate passively, rather than in response to energy received from a control unit. In particular, each barrier 28b-28h can be formed from a material that will dissolve after a certain amount of time once the catheter 10 is implanted within the body. The barriers 28b-28h closest to the distal-most end 16b of the catheter 10 would preferably dissolve before the barriers 28b-28h positioned near the proximal end 16a. Alternatively, the barriers 28b-28h can be formed from a material that dissolves when placed into contact with a biocompatible solvent, such that the solvent can be injected into the device 10 when a blockage occurs. In an exemplary embodiment, each row of barriers 28b-28h would dissolve in response to a different biocompatible solvent to allow only a single row 26a-26h of barriers 28b-28h to be dissolved when necessary.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable fluid management device, comprising:
   a catheter having a proximal end, a distal end, and an inner lumen extending therethrough;
   a plurality of fluid entry ports formed in a sidewall of the catheter and in fluid communication with the inner lumen of the catheter; and
   at least one fluid-impermeable barrier disposed in and occluding selected fluid entry ports, the at least one barrier being coupled to at least one conductor that is effective to deliver an electric current to the at least one barrier to selectively remove the barrier with respect to selected fluid entry ports.

2. The device of claim 1, wherein the barrier is selected from the group consisting of a membrane, a cap, a plug, and a film.

3. The device of claim 1, further comprising:
   a microprocessor coupled to the catheter and effective to selectively control the application of an electric current to one or more of the barriers to remove the barrier; and
   a plurality of conductors effective to carry the electric current, each conductor extending from the microprocessor to one or more of the barriers.

4. The device of claim 3, wherein the microprocessor is effective to initiate removal of the barrier in response to a signal received from a remote device.

5. The device of claim 3, further comprising a sensor disposed adjacent to one or more of the selected fluid entry ports, the microprocessor being effective to initiate removal of the barrier upon detection of a particular condition detected by the sensor.

6. The device of claim 3, wherein the barrier is formed from a material selected from the group consisting of copper, gold, silver, zinc, and conductive polymers or copolymers.

7. The device of claim 1, wherein the plurality of fluid entry ports are arranged in rows that extend around a diameter of the catheter and that are positioned longitudinally apart from one another, each row including at least one fluid entry port.

8. The device of claim 7, further comprising a microprocessor coupled to the catheter effective to selectively remove the barrier on each fluid entry port in a particular row by controlling the application of an electric current to the barrier through the at least one conductor, each conductor extending from the microprocessor to one or more of the barriers.

9. The device of claim 7, further comprising a plurality of filter members, each filter member extending transversely to a longitudinal axis of the catheter member and being positioned between two rows of fluid entry ports.

10. The device of claim 1, further comprising a filter material disposed around an inner diameter of the catheter and extending between the proximal and distal ends of the catheter.

11. A method of maintaining fluid flow through a catheter, comprising:
   detecting a blockage of fluid-flow through a distal-most barrier-free row of fluid entry ports in a catheter;
   activating a control member to send an electric current through at least one conductor to disintegrate at least one barrier from at least one fluid entry ports positioned just proximal to the distal-most row of fluid entry ports; and
   repeating the steps of detecting and activating as necessary.

12. The method of claim 11, wherein a microprocessor is coupled to the control member and initiates disintegration of the barrier in response to a signal from a remote device.

13. The method of claim 11, wherein a sensor disposed adjacent to one or more of the fluid ports detects a blockage of fluid-flow and communicates with the microprocessor to initiate disintegration of the barrier.

14. An implantable fluid management device, comprising:
a catheter having a proximal end, a distal end, and an inner lumen extending therethrough;
a plurality of fluid entry ports formed in a sidewall of the catheter and in fluid communication with the inner lumen of the catheter; and
a fluid-impermeable barrier coupled to the sidewall and occluding at least one of the fluid entry ports, the barrier being coupled to an energy source that is adapted to deliver energy to the barrier to selectively disintegrate the barrier with respect to the at least one fluid entry ports.

* * * * *